(12) United States Patent
Akamine et al.

(10) Patent No.: US 10,130,710 B2
(45) Date of Patent: Nov. 20, 2018

(54) FORMULATION AND METHOD FOR PRODUCING SAME

(71) Applicant: SEKISUI CHEMICAL CO., LTD., Osaka, Osaka (JP)

(72) Inventors: Takayuki Akamine, Osaka (JP); Kazushi Itou, Osaka (JP); Saori Tone, Osaka (JP); Yoshiko Abe, Tokyo (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 15/502,754

(22) PCT Filed: Sep. 18, 2015

(86) PCT No.: PCT/JP2015/076762
§ 371 (c)(1),
(2) Date: Feb. 8, 2017

(87) PCT Pub. No.: WO2016/043323
PCT Pub. Date: Mar. 24, 2016

(65) Prior Publication Data
US 2017/0232106 A1    Aug. 17, 2017

(30) Foreign Application Priority Data

| Sep. 19, 2014 | (JP) | 2014-191274 |
| Oct. 17, 2014 | (JP) | 2014-213069 |
| Mar. 24, 2015 | (JP) | 2015-061771 |
| Jun. 29, 2015 | (JP) | 2015-130489 |
| Jun. 29, 2015 | (JP) | 2015-130493 |

(51) Int. Cl.

| *A61K 47/26* | (2006.01) |
| *A61K 47/06* | (2006.01) |
| *A61K 47/14* | (2017.01) |
| *A61K 9/10*  | (2006.01) |
| *A61K 31/13* | (2006.01) |
| *A61K 9/00*  | (2006.01) |
| *A61K 45/06* | (2006.01) |
| *A61K 9/14*  | (2006.01) |
| *A61K 9/16*  | (2006.01) |
| *A61K 9/50*  | (2006.01) |
| *A61K 31/445*| (2006.01) |
| *A61K 31/47* | (2006.01) |
| *A61K 31/53* | (2006.01) |

(52) U.S. Cl.
CPC ............ *A61K 47/26* (2013.01); *A61K 9/0014* (2013.01); *A61K 9/10* (2013.01); *A61K 9/145* (2013.01); *A61K 9/1617* (2013.01); *A61K 9/1623* (2013.01); *A61K 9/5015* (2013.01); *A61K 31/13* (2013.01); *A61K 31/445* (2013.01); *A61K 31/47* (2013.01); *A61K 31/53* (2013.01); *A61K 45/06* (2013.01); *A61K 47/06* (2013.01); *A61K 47/14* (2013.01)

(58) Field of Classification Search
CPC ...... A61K 47/26; A61K 45/06; A61K 31/445; A61K 9/5015; A61K 9/1623; A61K 9/1617; A61K 31/53; A61K 31/47; A61K 9/0014; A61K 9/145; A61K 31/13; A61K 9/10; A61K 47/14; A61K 47/06
See application file for complete search history.

(56) References Cited

U.S. PATENT DOCUMENTS

| 2003/0157326 | A1* | 8/2003 | Vaghefi ............... A61K 9/1617 428/402.2 |
| 2007/0207138 | A1  | 9/2007 | Goto et al. |
| 2008/0254077 | A1* | 10/2008 | Prigent ................... A61K 8/11 424/401 |
| 2009/0238846 | A1  | 9/2009 | Fujii et al. |
| 2010/0298447 | A1  | 11/2010 | Fujii et al. |
| 2014/0296338 | A1  | 10/2014 | Hirano et al. |

FOREIGN PATENT DOCUMENTS

| EP | 2 305 292 A1 | 4/2011 |
| EP | 3 235 493 A1 | 10/2017 |
| JP | 2-35048 A | 2/1990 |
| JP | 9-268234 A | 10/1997 |
| JP | 2013-202005 A | 10/2013 |
| WO | WO-2005/094789 A1 | 10/2005 |
| WO | WO-2006/025583 A1 | 3/2006 |
| WO | WO-2009/057808 A1 | 5/2009 |
| WO | WO-2013/031729 A1 | 3/2013 |
| WO | WO-2017/002865 A1 | 1/2017 |
| WO | WO-2017/014306 A1 | 1/2017 |

OTHER PUBLICATIONS

International Search Report for the Application No. PCT/JP2015/076762 dated Dec. 15, 2015.
Written Opinion of the International Searching Authority (PCT/ISA/237) for Application No. PCT/JP2015/076762 dated Dec. 15, 2015.
Written Opinion of the International Searching Authority (PCT/ISA/237) for Application No. PCT/JP2015/076762 dated Dec. 15, 2015 (English Translation dated Mar. 30, 2017).
Supplementary European Search Report for the Application No. EP 15 84 1975 dated Jan. 25, 2018.
Extended European Search Report for Application No. EP 17 19 4793 dated Jan. 30, 2018.

(Continued)

*Primary Examiner* — Robert A Wax
*Assistant Examiner* — Quanglong N Truong
(74) *Attorney, Agent, or Firm* — Cheng Law Group, PLLC

(57) ABSTRACT

An object is to provide a formulation that includes a particle containing an active ingredient and a surfactant, and a base, and is more excellent in storage stability. For solution, a formulation including a particle containing an active ingredient and a surfactant, and a base, in which the surfactant is contained in a ratio of 5 to 100 parts by weight based on 1 part by weight of the active ingredient, is provided.

17 Claims, No Drawings

(56) References Cited

OTHER PUBLICATIONS

Kitaoka, Momoko et al., "Needle-free immunization using a sold-in-oil nanodispersion enhanced by a skin-permeable oligoarginine peptide", International Journal of Pharmaceutics, 2013, vol. 458, pp. 334-339. (XP028782907).

Martins, Madalena et al., "In vitro and computational studies of transdermal perfusion of nanoformulations containing a large molecular weight protein", Colloids and Surfaces B: Biointerfaces, 2013, vol. 108, pp. 271-278. (XP028593445).

Tahara, Yoshiro et al., "A solid-in-oil nanodispersion for transcutaneous protein delivery", Journal of Controlled Release, 2008, vol. 131, pp. 14-18. (XP025506363).

Piao, Hongyu et al., "A Novel Solid-in-oil Nanosuspension for Transdermal Delivery of Diclofenac Sodium", Pharmaceutical Research, 2008, vol. 25, No. 4, pp. 898-901. (XP019613044).

\* cited by examiner

FORMULATION AND METHOD FOR PRODUCING SAME

TECHNICAL FIELD

The present invention relates to a formulation and a method for producing the same.

BACKGROUND ART

Formulations each including a particle containing an active ingredient and a surfactant, and a base are used in a wide range of applications such as medicines, food and cosmetics.

As an example of the formulations used in the applications such as medicines, food and cosmetics, a formulation having a core-shell structure in which a core portion contains the active ingredient and a shell portion contains the surfactant has been proposed (Patent Literature 1).

CITATION LIST

Patent Literature

Patent Literature 1: International Publication No. WO2006/025583

SUMMARY OF INVENTION

Technical Problem

The present inventors have found, through independent studies, that there still is room for improvement in storage stability of the above-described formulations produced by a conventional production method.

An object of the present invention is to provide a formulation that includes a particle containing an active ingredient and a surfactant, and a base, and is more excellent in the storage stability.

Solution to Problem

The present inventors made earnest studies to solve the above-described problem, resulting in finding that the problem can be solved by setting a content of the surfactant in the formulation to a specific range based on the active ingredient. The present invention was accomplished through various attempts made based on this finding, and embraces the following aspects.

Aspect 1.

A formulation including: a particle containing at least one active ingredient and at least one surfactant; and a base, in which the surfactant is contained in total in a ratio of 5 to 100 parts by weight based on 1 part by weight of the active ingredient in total.

Aspect 2.

The formulation according to aspect 1, in which the base has a water-octanol partition coefficient of 6.5 to 17.0.

Aspect 3.

The formulation according to aspect 1 or 2, in which the base contains:

(a) an ester compound containing at least two, in total, hydrocarbon groups, each having 5 or more carbon atoms in a longest straight-chain portion thereof, of at least one selected from the group consisting of an alkyl group, an alkenyl group and an alkynyl group, a difference in the number of carbon atoms, in the longest straight-chain portion thereof among the hydrocarbon groups, respectively having longest and shortest longest straight-chain portions being smaller than 5; and/or (b) a hydrocarbon having 12 or more carbon atoms.

Aspect 4.

The formulation according to aspect 3, in which the ester compound and the hydrocarbon have a solubility parameter (SP value) of 6.5 to 10 $(cal/cm^3)^{1/2}$.

Aspect 5.

The formulation according to aspect 3 or 4, in which the ester compound is at least one ester compound selected from the group consisting of isononanoic acid esters, triglycerides and glycol fatty acid esters.

Aspect 6.

The formulation according to aspect 3 or 4, in which the ester compound is at least one ester compound selected from the group consisting of isononyl isononanoate, isotridecyl isononanoate, neopentyl glycol diisononanoate, triethylhexanoin and triheptanoin.

Aspect 7.

The formulation according to any one of aspects 1 to 6, in which the surfactant has a weighted average value of an HLB value of 10 or less.

Aspect 8.

The formulation according to any one of aspects 1 to 7, in which the surfactant has an alkyl chain.

Aspect 9.

The formulation according to any one of aspects 1 to 8, in which the surfactant is at least one surfactant selected from the group consisting of sucrose fatty acid esters, glycerin fatty acid esters, polyoxyethylene glycerin fatty acid esters, sorbitan fatty acid esters, polyoxyethylene sorbitol fatty acid esters, polyoxyethylene castor oil and hydrogenated castor oil.

Aspect 10.

The formulation according to any one of aspects 1 to 9, in which the active ingredient contains a compound having a hydrophilic group and a hydrophobic group, and the surfactant contains a surfactant having a melting point of 30° C. or more.

Aspect 11.

The formulation according to aspect 10, in which the surfactant having a melting point of 30° C. or more is a sucrose fatty acid ester.

Aspect 12.

The formulation according to aspect 11, in which the sucrose fatty acid ester is an ester of a sucrose and a saturated or unsaturated monovalent fatty acid having 8 to 30 carbon atoms.

Aspect 13.

The formulation according to aspect 11 or 12, in which the sucrose fatty acid ester is at least one sucrose fatty acid ester selected from the group consisting of sucrose palmitic acid esters, sucrose oleic acid esters and sucrose behenic acid esters.

Aspect 14.

The formulation according to any one of aspects 1 to 9, in which the active ingredient contains a readily crystallizable compound, and the surfactant contains a surfactant having a melting point of −40° C. or more in a ratio of 5 to 100 parts by weight based on 1 part by weight of the readily crystallizable compound.

Aspect 15.

The formulation according to aspect 14, in which the surfactant is a sucrose fatty acid ester.

Aspect 16.

The formulation according to aspect 15, in which the sucrose fatty acid ester is an ester of a sucrose and a saturated and/or unsaturated monovalent fatty acid having 8 to 30 carbon atoms.

Aspect 17.

The formulation according to aspect 15 or 16, in which the sucrose fatty acid ester is at least one sucrose fatty acid ester selected from sucrose lauric acid esters, sucrose oleic acid esters and sucrose erucic acid esters.

Advantageous Effect of Invention

The present invention can provide a formulation that includes a particle containing an active ingredient and a surfactant, and a base, and is excellent in storage stability.

DESCRIPTION OF EMBODIMENT

1. Composition of Formulation

A formulation of the present invention contains at least the following particle.

1.1 Particle

The particle contains at least one active ingredient and at least one surfactant. More specifically, the particle is composed of at least two fractions, that is, a first fraction containing an active ingredient and a second fraction containing a surfactant. Since the particle has such a composition, when the formulation of the present invention is applied to, for example, skin, the active ingredient contained in the first fraction can be slowly released.

It is noted that the first fraction and the second fraction are not especially limited in their positional relationship as long as they are bound to each other to form an aggregate.

In one aspect, a part or the whole of a surface of the first fraction is coated with the second fraction in the particle. A more specific example of this aspect includes a core-shell structure in which the first fraction corresponds to a core portion and the second fraction corresponds to a shell portion subsuming the core portion. It is noted that there is no need to cover the whole surface of the core portion with the shell portion in the core-shell structure of the present invention.

In another aspect, the first fraction an the second fraction are mixed with each other in the particle.

From the viewpoint of the absorbency of the active ingredient, the particle of the present invention has a water content of preferably 20% by weight or less, more preferably 5% by weight or less, and further preferably 1% by weight or less although this is not restrictive.

1.1.1 First Fraction

The first fraction contains at least the active ingredient.

When the active ingredient is a drug, either one capable of achieving systemic action or one capable of achieving local action can be used.

The active ingredient is not especially limited and can be selected from a wide range.

1.1.1.1 Hydrophilic Active Ingredient

An example of the active ingredient includes a hydrophilic compound.

When the active ingredient is hydrophilic, such a compound typically has the following features although this is not restrictive:

a molecular weight of 1,000,000 or less; and an octanol-water partition coefficient of −8 to 6.

In the above-described features, the molecular weight is preferably 10,000 or less, more preferably 5,000 or less, and further preferably 2,000 or less. The lower limit of the molecular weight is not especially limited, and is generally 50 or more.

In the above-described features, the octanol-water partition coefficient is preferably −6 to 5, and more preferably −5 to 4.

Incidentally, the octanol-water partition coefficient herein is obtained by adding a target component to be measured into a flask charged with n-octanol and an aqueous buffer of pH 7 or water, shaking the resultant, and performing calculation, in accordance with the following equation, based on active ingredient concentrations in respective phases.

$$\text{Octanol-water partition coefficient} = \text{Log}_{10}(\text{concentration in octanol phase/concentration in aqueous phase})$$

When the active ingredient is a drug, one capable of achieving systemic action or local action is suitably used although this is not restrictive.

Specific examples of the drug are not especially limited but include dementia treatment drugs such as memantine, donepezil, rivastigmine and galantamine, antiepileptic drugs, antidepressants, anti-Parkinson's disease drugs, antiallergic drugs, anti-cancer drugs, antidiabetic drugs, antihypertensive agents, ED treatment drugs, dermatological agents, local anesthetics, and osteoporosis treatment drugs, as well as nasal drops, eye drops, oral cavity agent and suppositories, and pharmaceutically acceptable salts thereof. The pharmaceutically acceptable salts are not especially limited, and examples include hydrochlorides such as memantine hydrochloride and donepezil hydrochloride, tartrates such as rivastigmine tartrate, and hydrobromides such as galantamine hydrobromide.

In the application to cosmetics, the active ingredient is not especially limited as long as it can achieve skin permeability, and examples include vitamin components such as vitamin C and vitamin E, moisturizing ingredients such as hyaluronic acid, ceramide and collagen, skin-whitening ingredients such as tranexamic acid and arbutin, hair-growing ingredients such as minoxidil, beauty ingredients such as FGF (fibroblast growth factor) and EGF (epidermal growth factor), and salts and derivatives thereof.

1.1.1.2 Active Ingredient Having No Surface Activity

Another example of the active ingredient includes a compound having no surface activity (non-surface active compound).

In the present invention, it is determined as follows whether or not a given compound has surface activity. When a target compound is dissolved, in a ratio of 0.5% by weight, in 100 ml of pure water at room temperature and the resulting solution is stirred at 500 rpm, if bubbles are observed, the compound is determined to have surface activity, and if bubbles are not observed, the compound is determined not to have surface activity.

The non-surface active compound is not especially limited, and a variety of compounds can be used, and a compound having a water-octanol partition coefficient of −6 to 6 is preferably used from the viewpoint of the effect of the present invention. From this point of view, a non-surface active compound having a water-octanol partition coefficient of −3 to 6 is particularly preferably used.

The non-surface active compound is not especially limited, and in the application to a drug, specific examples include donepezil, vardenafil, fesoterodine, octreotide, gabapentin, risedronate, and pharmaceutically acceptable salts thereof. The pharmaceutically acceptable salts thereof are not especially limited, and examples include donepezil hydrochloride, vardenafil hydrochloride hydrate, fesoterodine fumarate, octreotide hydrochloride and sodium risedronate hydrate.

1.1.1.3 Active Ingredient of Readily Crystallizable Compound

Another example of the active ingredient includes a readily crystallizable compound.

The readily crystallizable compound is not especially limited as long as it is a compound that can be in the form of a crystal in the first fraction of the present invention.

An example of the readily crystallizable compound includes a compound having a characteristic that it is liable to change into a needle shape when recrystallized.

The readily crystallizable compound may be a compound that is in the form of a needle crystal in the first fraction of the present invention.

Specific examples of the readily crystallizable compound are not especially limited, but include, in the application to a drug for example, memantine or a salt thereof, depogen and aspirin.

When the readily crystallizable compound is a drug, any of the pharmaceutically acceptable salts can be used as the compound.

1.1.1.4 Active Ingredient of Compound Having Hydrophilic Group and Hydrophobic Group Another example of the active ingredient includes a compound having a hydrophilic group and a hydrophobic group.

The compound having a hydrophilic group and a hydrophobic group is not especially limited.

Without being constrained by theory, the compound having a hydrophilic group and a hydrophobic group can exert an effect as a surfactant.

The compound having a hydrophilic group and a hydrophobic group is typically a compound having at least one of the following features (1) to (3):

(1) a molecular weight of 100 to 10,000;
(2) water solubility of 0.1% to 100%; and
(3) an HLB value of 0 to 7 or 10 to 20.

In the above-described features, the molecular weight is preferably 100 to 5,000, and more preferably 100 to 1,000.

In the above-described features, the water solubility is preferably 1% to 50%, and more preferably 5% to 50%.

In the above-described features, the HLB value is preferably 0 to 5, and more preferably 0 to 3.

It is noted that the water solubility herein refers to a value based on an EPA method (EPA Chemical Fate Testing Guideline CG-1500 "Water Solubility").

Specific examples of the compound having a hydrophilic group and a hydrophobic group are not especially limited, and include, in the application to a drug for example, montelukast, benzalkonium chloride, dehydrocholic acid and polidocanol.

When the compound having a hydrophilic group and a hydrophobic group is a drug, any of the above-described pharmaceutically acceptable salts can be used as the compound.

Other specific examples of the compound having a hydrophilic group and a hydrophobic group include cosmetic preparations and perfume preparations, for example.

1.1.1.5 Detailed General Description of First Fraction

An amount of the active ingredient contained in the particle depends on the type of active ingredient, and can be, for example, 0.1 to 50% by weight based on the entire particle.

The first fraction may contain two or more active ingredients if necessary. In this case, the formulation of the present invention can be used as a combination drug.

The first fraction may further contain at least one additional component in addition to the active ingredient.

The additional component is not especially limited, and examples include a stabilizer, an absorption promoter, a stimulation reducing agent and an antiseptic.

The stabilizer has an effect of stabilizing the structure of the particle, and works to ensure the slow-release effect of the active ingredient by preventing unintended early disintegration of the particle.

The stabilizer is not especially limited, and specific examples include polysaccharides, proteins and hydrophilic polymer materials. One, two or more of these stabilizers may be contained. A content of the stabilizer in the first fraction depends on the type of stabilizer and can be appropriately set, and for example, it may be contained to attain a weight ratio between the active ingredient and the stabilizer of 100:1 to 1:10.

The absorption promoter is not especially limited, and specific examples include higher alcohols, N-acyl sarcosine and a salt thereof, higher monocarboxylic acids, higher monocarboxylic acid esters, aromatic monoterpene fatty acid esters, divalent carboxylic acids having 2 to 10 carbon atoms and salts thereof, polyoxyethylene alkyl ether phosphates and salts thereof, lactic acid, lactic acid esters and citric acid, and the like. One, two or more of these absorption promoters may be contained. A content of the absorption promoter in the core portion depends on the type of absorption promoter and may be appropriately set, and it may be contained, for example, to attain a weight ratio between the active ingredient and the absorption promoter of 100:1 to 1:50.

The stimulation reducing agent is not especially limited, and specific examples include hydroquinone glycosides, pantethine, tranexamic acid, lecithin, titanium oxide, aluminum hydroxide, sodium nitrite, sodium hydrogen sulfite, soy lecithin, methionine, glycyrrhizic acid, BHT, BHA, vitamin E and derivatives thereof, vitamin C and derivatives thereof, benzotriazole, propyl gallate, and mercaptobenzimidazole. One, two or more of these stimulation reducing agents may be contained. A content of the stimulation reducing agent in the first fraction depends on the type of stimulation reducing agent and may be appropriately set, and it may be contained in a content of, for example, 0.1% to 50%.

The antiseptic is not especially limited, and specific examples include methyl parahydroxybenzoate, propyl parahydroxybenzoate, phenoxyethanol, benzalkonium chloride, and thymol. A content of the antiseptic in the first fraction depends on the type of antiseptic and may be appropriately set, and it may be contained in a content of, for example, 0.01% to 10%. One, two or more of these antiseptics may be contained.

1.1.2 Second Fraction

The second fraction contains at least one surfactant.

The formulation of the present invention has a characteristic that it contains the surfactant in total in a ratio of 5 to 100 parts by weight based on 1 part by weight of the active ingredient in total. Owing to this characteristic, the formulation of the present invention is excellent in storage stability.

The formulation of the present invention may contain a plurality of surfactants.

A surfactant having a weighted average value of the HLB value of 10 or less, preferably 5 or less, and more preferably 3 or less can be used.

From the viewpoint of absorbency, the surfactant has a melting point of preferably 50° C. or less and more preferably 40° C. or less.

As the surfactant, one having a weighted average value of the HLB value of 10 or less and a melting point of 50° C. or less can be preferably used, one having a weighted average value of the HLB value of 5 or less and a melting point of 50° C. or less can be more preferably used, and one having a weighted average value of the HLB value of 5 or less and a melting point of 40° C. or less can be further more preferably used.

The HLB (Hydrophile Lypophile Balance) value of the present invention can be a parameter used for determining whether an emulsifier is hydrophilic or lipophilic, and takes a value from 0 to 20.

A smaller HLB value means stronger lipophilicity. In the present invention, this value is calculated in accordance with the following Griffin equation:

$$\text{HLB value} = 20 \times \{(\text{molecular weight of hydrophilic portion})/(\text{total molecular weight})\}$$

The weighted average value of the HLB value is calculated as follows.

For example, assuming that surfactant materials respectively having HLB values A, B and C are used, and that charged weights thereof in synthesis of the particle are respectively x, y and z, the weighted average value is calculated as follows:

$$\text{Weight average value} = (xA + yB + zC)/(x + y + z)$$

Besides, the melting point of the present invention is obtained based on an endothermic peak obtained in measurement with a differential scanning calorimeter (DSC).

The surfactant is not especially limited but can be appropriately selected in accordance with the use. For example, the surfactant can be widely selected from, for example, those usable as external drugs and cosmetics.

The surfactant may be any of a nonionic surfactant, an anionic surfactant, a cationic surfactant and an amphoteric surfactant.

The nonionic surfactant is not especially limited, and examples include fatty acid esters, fatty alcohol ethoxylates, polyoxyethylene alkyl phenyl ethers, alkyl glycosides, and fatty acid alkanolamide.

The fatty acid esters are not especially limited but are preferably sugar fatty acid esters. In particular, sucrose fatty acid esters are preferred. Specific examples include esters of fatty acids, such as erucic acid, oleic acid, lauric acid, stearic acid and behenic acid, and sucrose.

Other fatty acid esters are not especially limited, and examples include esters of at least one of glycerin, polyglycerin, polyoxyethylene glycerin, sorbitan and polyoxyethylene sorbitol, and a fatty acid. In particular, polyglycerin fatty acid esters are preferred.

Examples of the anionic surfactants include alkyl sulfate salts, polyoxyethylene alkyl ether sulfate salts, alkyl benzene sulfonate salts, fatty acid salts and phosphate salts.

Examples of the cationic surfactants include alkyl trimethyl ammonium salts, dialkyl dimethyl ammonium salts, alkyl dimethyl benzyl ammonium salts and amine salts.

Examples of the amphoteric surfactants include alkyl amino fatty acid salts, alkyl betaines and alkyl amine oxides.

A mixing amount of the surfactant can be appropriately set within a range where the effect of the present invention is exhibited, and for example, a weight ratio to the active ingredient can be 1:5 to 1:100. In this case, the formulation of the present invention is excellent in the absorbency. From this point of view, the weight ratio to the active ingredient is preferably 1:5 to 1:50, and more preferably 1:10 to 1:30.

The surfactant may have an alkyl chain although this is not restrictive. The length of the alkyl chain is not especially limited, and can be widely selected from a range of 8 to 30, and is particularly preferably 10 to 24.

In the case where merely a surfactant having an alkyl chain is used, or where a surfactant having an alkyl chain is used in combination with another surfactant, when a weight ratio of alkyl chains contained in total between the active ingredient and the surfactant(s) 1:1 to 1:70, the formulation of the present invention is excellent in the absorbency. From this point of view, the weight ratio is preferably 1:2 to 1:50.

The second fraction may further contain, in addition to the surfactant, at least one additional component. The additional component is not especially limited, and examples include a stimulation reducing agent, an analgesic, an absorption promoter, a stabilizer and an antiseptic.

The stimulation reducing agent is not especially limited, and specific examples include hydroquinone glycosides, pantethine, tranexamic acid, lecithin, titanium oxide, aluminum hydroxide, sodium nitrite, sodium hydrogen sulfite, soy lecithin, methionine, glycyrrhizic acid, BHT, BHA, vitamin E and derivatives thereof, vitamin C and derivatives thereof, benzotriazole, propyl gallate, and mercaptobenzimidazole. One, two or more of these stimulation reducing agents may be contained. A content of the stimulation reducing agent in the second fraction depends on the type of stimulation reducing agent and may be appropriately set, and it may be contained in a content of, for example, 0.1% to 50%.

The analgesic is not especially limited, and specific examples include local anesthetics such as procaine, tetracaine, lidocaine, dibucaine and prilocaine, and salts thereof. One, two or more of the analgesics may be contained. A content of the analgesic in the second fraction depends on the type of analgesic and can be appropriately set, and it may contained in a content of, for example, 0.1% to 30%.

The absorption promoter is not especially limited, and specific examples include higher alcohols, N-acyl sarcosine and a salt thereof, higher monocarboxylic acids, higher monocarboxylic acid esters, aromatic monoterpene fatty acid esters, divalent carboxylic acids having 2 to 10 carbon atoms and salts thereof, polyoxyethylene alkyl ether phosphates and salts thereof, lactic acid, lactic acid esters and citric acid. One, two or more of these absorption promoters may be contained. A content of the absorption promoter in the second fraction depends on the type of absorption promoter and may be appropriately set, and it may be contained in a content of, for example, 0.1% to 30%.

The stabilizer has an effect of stabilizing the structure of the particle, and works to ensure the slow-release effect of the drug by preventing unintended early disintegration of the particle.

The stabilizer is not especially limited, and specific examples include fatty acids and salts thereof, parahydroxybenzoic acid esters such as methylparaben and propylparaben, alcohols such as chlorobutanol, benzyl alcohol and phenyl ethyl alcohol, thimerosal, acetic anhydride, sorbic acid, sodium hydrogen sulfite, L-ascorbic acid, sodium ascorbate, butyl hydroxy anisole, butyl hydroxy toluene, propyl gallate, tocopherol acetate, dl-α-tocopherol, proteins and polysaccharides. One, two or more of the stabilizers may be contained. A content of the stabilizer in the second fraction depends on the type of stabilizer and may be appropriately set, and it can be contained, for example, to attain a weight ratio between the surfactant and the stabilizer of 1:0.01 to 1:50.

The antiseptic is not especially limited, and specific examples include methyl parahydroxybenzoate, propyl parahydroxybenzoate, phenoxyethanol, and thymol. One, two or more of the antiseptics may be contained. A content of the antiseptic in the second fraction depends on the type of antiseptic and may be appropriately set, and it may be contained in a content of, for example, 0.01% to 10%.

1.1.2.1 Case of Active Ingredient Containing Non-Surface Active Compound

In a case where the active ingredient contains a non-surface active compound, a total mixing amount of surfactants can be appropriately set within a range where the effect of the present invention can be exhibited, and for example, a weight ratio to the non-surface active compound contained in the particle can be 1:5 to 1:100, more preferably 1:10 to 1:70, and further preferably 1:10 to 1:30.

1.1.2.2 Case of Active Ingredient Containing Readily Crystallizable Compound

In a case where the active ingredient contains a readily crystallized compound, the following surfactant is preferred:

A surfactant having a melting point of −40° C. or more, more preferably −10 to 60° C. is contained in an amount of 5 to 100 parts by weight based on 1 part by weight of the readily crystallizable compound. In this manner, the crystal growth over time of the readily crystallizable compound in the first fraction is suppressed, so that the particle can be stabilized for a long period of time. In a preferred aspect, owing to this feature of the second fraction, the crystal growth over time of the readily crystallizable compound is suppressed during storage at a low temperature (of, for example, 4° C. or less), so that the particle can be stabilized for a long period of time.

The second fraction contains a surfactant having a melting point of −40° C. or more in an amount of preferably 10 to 70 parts by weight based on 1 part by weight of the readily crystallizable compound. In this manner, a particle in a particulate shape stabilized for a long period of time can be obtained. From this point of view, the second fraction more preferably contains the surfactant having a melting point of −40° C. or more in an amount of 15 to 50 parts by weight based on 1 part by weight of the readily crystallizable compound.

The second fraction may contain a plurality of surfactants. In this case, the second fraction may contain, as the surfactants, a plurality of merely surfactants having a melting point of −40° C. or more, or one, two or more surfactants having a melting point lower than 30° C. in addition to a surfactant having a melting point of −40° C. or more.

When the second fraction contains, in addition to the surfactant having a melting point of −40° C. or more, the surfactant(s) having a melting point lower than 30° C., a ratio of the former can be 0.5% by weight to 20% by weight, and more preferably 1% by weight to 10% by weight based on the total amount of the surfactants.

Although this is not restrictive, in a case where a solution in which a second fraction component containing the surfactant is dissolved in a solvent such as cyclohexane, hexane or toluene is used for producing the particle as described later, when the second fraction component contains a surfactant having a melting point lower than 30° C. in addition to a surfactant having a melting point of −40° C. or more, the surfactants are advantageously readily dissolved in the solvent.

The surfactant having a melting point of −40° C. or more is not especially limited, and a specific example includes a sucrose fatty acid ester.

The sucrose fatty acid ester is not especially limited, and an ester of sucrose and a saturated or unsaturated monovalent fatty acid having 8 to 30 carbon atoms can be used.

Specific examples of the sucrose fatty acid ester are not especially limited, and include sucrose lauric acid esters, sucrose oleic acid esters and sucrose erucic acid esters.

As the sucrose fatty acid ester, a plurality of sucrose fatty acid esters may be used together.

The surfactant having a melting point of −40° C. or more is not especially limited, and one having an HLB value of 10 or less, and preferably 7 or less can be used.

A total mixing amount of the surfactant(s) can be appropriately set within the range where the effect of the present invention can be exhibited, and for example, a weight ratio to the readily crystallizable compound contained in the first fraction can be 1:5 to 1:100, more preferably 1:10 to 1:70, and further preferably 1:15 to 1:50.

1.1.2.3 Case of Active Ingredient Containing Compound Having Hydrophilic Group and Hydrophobic Group When the active ingredient contains a compound having a hydrophilic group and a hydrophobic group, a surfactant having a melting point of 30° C. or more is preferably contained as the surfactant.

The second fraction may contain a plurality of surfactants together. In this case, the second fraction may contain, as the surfactants, a plurality of merely surfactants having a melting point of 30° C. or more, or may contain one, two or more surfactants having a melting point lower than 30° C. in addition to a surfactant having a melting point of 30° C. or more.

When the second fraction contains, in addition to the surfactant having a melting point of 30° C. or more, the surfactant(s) having a melting point lower than 30° C., a ratio of the former can be 0.5% by weight to 20% by weight, and more preferably 1% by weight to 10% by weight based on the total amount of the surfactants.

Although this is not restrictive, in a case where a solution in which a second fraction component containing a surfactant is dissolved in a solvent such as cyclohexane, hexane or toluene is used for producing the particle of the present invention as described later, when the second fraction component contains a surfactant having a melting point lower than 30° C. in addition to a surfactant having a melting point of 30° C. or more, the surfactants are advantageously readily dissolved in the solvent.

The surfactant having a melting point of 30° C. or more is not especially limited, and a specific example includes a sucrose fatty acid ester.

The sucrose fatty acid ester is not especially limited, and preferably an ester of sucrose and a saturated or unsaturated monovalent fatty acid having 8 to 30 carbon atoms can be used.

Specific examples of the sucrose fatty acid ester are not especially limited, and preferably include sucrose palmitic acid esters, sucrose oleic acid esters and sucrose behenic acid esters.

As the sucrose fatty acid ester, a plurality of sucrose fatty acid esters may be used together.

The surfactant having a melting point of 30° C. or more is not especially limited, and one having an HLB value of preferably 7 or less, and more preferably 5 or less can be used.

A total mixing amount of the surfactants can be appropriately set within the range where the effect of the present invention can be exhibited, and for example, a weight ratio to the compound having a hydrophilic group and a hydrophobic group contained in the first fraction can be 1:5 to 1:100.

1.1.3 Base

The formulation of the present invention further contains the base. In a preferred aspect, the formulation of the present invention includes a phase containing the base (base phase), and the base phase contains at least the particle. In this case, the particle is dispersed in the base phase.

From the viewpoint of the storage stability, a solubility parameter (SP value), calculated in accordance with Okitsu's equation, of the base (a base having the largest weight ratio when a plurality of bases are contained) is preferably 6.5 to 10 $(cal/cm^3)^{1/2}$, and more preferably 7.0 to 9.5. When the solubility parameter is 12 or more, the particle may be disintegrated without being suspended in some cases.

It is noted that an SP value calculated in accordance with the Okitsu's equation is a parameter corresponding to hydrophilicity, and the Okitsu's equation is a method for calculating $\Delta F$ in the solubility parameter represented by the following equation (refer to Toshinao Okitsu, Journal of the Adhesion Society of Japan, vol. 29, No. 5, 204-211 (1993)).

$$\Delta\delta=\Delta F/\Delta V$$

wherein $\delta$ represents a solubility parameter, F represents a molar gravitational constant, and V represents a molar volume.

The base may contain an ester compound and/or a hydrocarbon.

An example of the ester compound includes an ester compound that has at least two, in total, hydrocarbon groups, each having 5 or more carbon atoms in a longest straight-chain portion thereof, of at least one selected from the group consisting of an alkyl group, an alkenyl group and an alkynyl group, and in which a difference in the number of carbon atoms in the longest straight-chain portion among the hydrocarbon groups, respectively having longest and shortest longest straight-chain portions is smaller than 5.

An example of the hydrocarbon includes a hydrocarbon having 12 or more carbon atoms and applicable to an external preparation.

When the ester compound and/or the hydrocarbon is contained in the base, a formulation excellent in the storage stability can be provided. Specifically, for example, a phenomenon in which the particle is changed in shape over time (for example, deformed into a wire-like shape or the like) can be suppressed. In this manner, the present invention is especially excellent in that the storage stability can be improved because the change in shape can be suppressed with viscosity and the like as the formulation satisfactorily retained.

In the present invention, an alkyl group, an alkenyl group or an alkynyl group means a group R or R' in an ester bond R—COO—R'. When the group R or R' contains an ester bond r-COO-r', however, it means a group r or r' positioned at the end. Besides, when the group r or r' contains another ester bond, it is similarly defined with the R and R' respectively read as the r and r'.

For example, triethyihexanoin has 3 alkyl groups, all of which have 6 carbon atoms in the main chain.

The number of carbon atoms of an alkyl group, an alkenyl group or an alkynyl group means, when the group is the group R in the ester bond R—COO—R', a value obtained by adding 1 to the number of carbon atoms of the main chain, and when the group is the group R', the number of carbon atoms itself of the main chain, respectively. The same shall apply to the groups r and r'.

An alkyl group, an alkenyl group or an alkynyl group may be linear or branched.

The length of the main chain of an alkyl group, an alkenyl group or an alkynyl group is not especially limited, and can be appropriately selected within a range where the effect of the present invention can be exhibited. The length of the main chain can be, for example, 2 to 20 or 2 to 15.

The ester compound contains preferably 2 to 4, and more preferably 2 to 3 alkyl groups, alkenyl groups or alkynyl groups.

From the viewpoint of the effect of the present invention, a water-octanol partition coefficient and/or hydrocarbon of the ester compound is preferably 6.5 to 17.0, more preferably 7.0 to 16.0, and further preferably 7.5 to 15.0. When the water-octanol coefficient is lower than 5.0, the particle may be disintegrated without being suspended in some cases.

Specific examples of the ester compound include isononanoic acid esters such as isononyl isononanoate, isotridecyl isononanoate and neopentyl glycol diisononanoate, and triglycerides such as triethylhexanoin and triheptanoin.

Specific examples of the hydrocarbon having 12 or more carbon atoms include liquid paraffin (mineral oil), heavy liquid isoparaffin, light liquid isoparaffin, $\alpha$-olefin oligomer, polyisobutene, hydrogenated polyisobutene, polybutene, squalane, olive-derived squalane, sugarcane-derived squalane, vaseline and solid paraffin. In particular, light liquid paraffin and liquid paraffin having 16 or more carbon atoms are more preferred because the viscosity is high and the stability of the formulation is improved when contained.

The formulation of the present invention may contain, as the base, combinations each of a plurality of ester compounds and a plurality of hydrocarbons.

Besides, the formulation of the present invention may contain a second base component different from both the ester compound and the hydrocarbon.

A mixing amount of the ester compound and/or the hydrocarbon contained in the base can be appropriately set within a range where the effect of the present invention can be exhibited, and it may be contained, for example, in a ratio of 10% to 100%, preferably 20% to 100% based on the whole base.

Now, a second base different from both the ester compound and the hydrocarbon will be described.

The second base is not especially limited, and can be widely selected from those usable as external drugs and cosmetics.

The second base is not especially limited, and can be appropriately selected from those suitable for dispersing the particle therein in accordance with the intended use or the like.

Besides, a plurality of second bases may be used together.

The second base is not especially limited, and examples include vegetable oils, animal oils, neutral lipids, synthetic fats and oils, sterol derivatives, waxes, monoalcohol carboxylic acid esters, hydroxy acid esters, polyhydric alcohol fatty acid esters, silicones, higher (polyhydric) alcohols, higher fatty acids and fluorine-based oils.

The vegetable oils are not especially limited, and examples include soy oil, sesame oil, olive oil, castor oil, balm oil, rice oil, cotton seed oil, sunflower oil, rice bran oil, cacao butter, cone oil, safflower oil and rapeseed oil.

The animal oils are not especially limited, and examples include mink oil, turtle oil, fish oil, cow oil, horse oil and pig oil.

The natural lipids are not especially limited, and examples include triolein, trilinolein, trimyristin, tristearin and triarachidonin.

The synthetic fats and oils are not especially limited, and examples include phospholipid and azone.

The sterol derivatives are not especially limited, and examples include dihydrocholesterol, lanosterol, dihydrolanosterol, fitosterol, cholic acid and cholesteryl linoleate.

Examples of the waxes include candelilla wax, carnauba wax, rice wax, Japan wax, beeswax, montan wax, ozokerite, ceresin, paraffin wax, microcrystalline wax, petrolatum, Fischer-Tropsch wax, polyethylene wax and an ethylene-propylene copolymer.

Examples of the monoalcohol carboxylic acid esters include octyldodecyl myristate, hexyldecyl myristate, octyldodecyl isostearate, cetyl palmitate, octyldodecyl palmitate, cetyl octoate, hexyldecyl octoate, octyl isononanoate, isodecyl neopentanoate, isotridecyl neopentanoate, isostearyl neopentanoate, octyldodecyl neodecanoate, oleyl oleate, octyldodecyl oleate, octyldodecyl ricinoleate, octyldodecyl lanolate, hexyldecyl dimethyloctanoate, octyldodecyl erucate, hydrogenated castor oil isostearate, ethyl oleate, ethyl avocado oil fatty acid, isopropyl myristate, isopropyl palmitate, octyl palmitate, isopropyl isostearate, isopropyl lanolin fatty acid, diethyl sebacate, diisopropyl sebacate, dioctyl sebacate, diisopropyl adipate, dibutyl octyl sebacate, diisobutyl adipate, dioctyl succinate and triethyl citrate.

Examples of the hydroxy acid esters include cetyl lactate, diisotearyl malate and hydrogenated castor oil monoisostearate.

Examples of the polyhydric alcohol fatty acid esters include glyceryl trioctanoate, glyceryl trioleate, glyceryl triisostearate, glyceryl diisostearate, glyceryl tri(caprylate/caprate), glyceryl tri(caprylate/caprate/myristate/stearate), hydrogenated rosin triglyceride (hydrogenated ester gum), rosin triglyceride (ester gum), glyceryl behenate eicosadioate, trimethylolpropane trioctanoate, trimethylolpropane triisostearate, neopentyl glycol dioctanoate, neopentyl glycol dicaprate, 2-butyl-2-ethyl-1,3-propanediol dioctanoate, propylene glycol dioleate, pentaerythrityl tetraoctanoate, hydrogenated rosin pentaerythrityl, ditrimethylolpropane triethylhexanoate, ditrimethylolpropane (isostearate/sebacate), pentaerythrityl triethylhexanoate, dipentaerythrityl (hydroxystearate/stearate/rosinate), diglyceryl diisostearate, polyglyceryl tetraisostearate, polyglyceryl-10 nonaisostearate, polyglyceryl-8 deca(erucate/isostearate/ricinoleate), diglyceryl oligoester (hexyldecanoate/sebacate), glycol distearate (ethylene glycol distearate), 3-methyl-1,5-pentanediol dineopentanoate and 2,4-diethyl-1,5-pentanediol dineopentanoate.

Examples of the silicones include dimethicone (dimethylpolysiloxane), highly polymerized dimethicone (highly polymerized dimethylpolysiloxane), cyclomethicone (cyclic dimethylsiloxane, decamethylcyclopentasiloxane), phenyl trimethicone, diphenyl dimethicone, phenyl dimethicone, stearoxypropyl dimethyl amine, (aminoethyl aminopropyl methicone/dimethicone) copolymer, dimethiconol, dimethiconol crosspolymer, silicone resin, silicone rubber, amino-modified silicone such as aminopropyl dimethicone or amodimethicone, cation-modified silicone, polyether-modified silicone such as dimethicone copolyol, polyglycerin-modified silicone, sugar-modified silicone, carboxylic acid-modified silicone, phosphoric acid-modified silicone, sulfuric acid-modified silicone, alkyl-modified silicone, fatty acid-modified silicone, alkyl ether-modified silicone, amino acid-modified silicone, peptide-modified silicone, fluorine-modified silicone, cation-modified or polyether-modified silicone, amino-modified or polyether-modified silicone, alkyl-modified or polyether-modified silicone, and polysiloxane-oxyalkylene copolymer.

Examples of the higher (polyhydric) alcohols include cetanol, myristyl alcohol, oleyl alcohol, lauryl alcohol, cetostearyl alcohol, stearyl alcohol, aralkyl alcohol, behenyl alcohol, jojoba alcohol, chimyl alcohol, selachyl alcohol, batyl alcohol, hexyldecanol, isostearyl alcohol, 2-octyl dodecanol and dimer diol.

Examples of the higher fatty acids include lauryl acid, myristic acid, palmitic acid, stearic acid, isostearic acid, behenic acid, undecylenic acid, 12-hydroxystearic acid, palmitoleic acid, oleic acid, linolic acid, linolenic acid, erucic acid, docosahexaenoic acid, eicosapentaenoic acid, isohexadecanoic acid, anteiso-heneicosanoic acid, long-chain branched fatty acid, dimer acid and hydrogenated dimer acid.

Examples of the fluorine-based oils include perfluorodecane, perfluorooctane and perfluoropolyether.

Other examples of the second base are not especially limited, but include bases used in ointments, creams, aerosols, tapes, patches, poultices, gels, nasal drops, eye drops, suppositories, oral agents and microneedles.

As the base, one appropriately containing another component may be used in addition to those exemplarily mentioned above. The base may further contain an additive having a gelling effect (a gelling agent) or the like.

Such an additive is not especially limited, and for example, hydrocarbons such as resins and silicones, amino acid, cyclic peptide, epoxy, rosin, melamine, pectins such as polysaccharides and surfactants, alginic acid, carrageenan, locust bean gum, guar gum, xanthan gum, dextrin fatty acid ester, inulin fatty acid ester, glycerin fatty acid ester and the like can be used. The resins are not especially limited, and examples include polyethylene, polypropylene, polyester, polystyrene and polyurethane. A base containing such a resin is not especially limited, and for example, a base containing such an additive in a ratio of 0.1 to 50%, preferably 1 to 30% can be used. Such a base is not especially limited, and for example, hydrocarbon-based bases such as liquid paraffin, cyclohexane, n-octane, toluene and xylene, and ester-based bases such as isopropyl myristate, isopropyl palmitate and cetyl ethylhexanoate are suitably used. A specific example of such a base includes, but is not limited to, a hydrocarbon gel ointment base such as Plastibase® (Bristol Myers Squibb) containing 95% of liquid paraffin and 5% polyethylene resin as a gelling agent.

1.1.3.1 Aspect where Drug-Containing Phase has High Viscosity

In the formulation of the present invention, the change in shape over time can be inhibited by setting the viscosity of a phase of the formulation where the particle containing a drug exists (which phase will be designated as the "drug-containing phase" in the present invention) to be higher than in a conventional formulation. Incidentally, features such as the viscosity of the drug-containing phase herein mentioned refer to the features of the drug-containing phase in a state taken out of the formulation of the present invention.

In the formulation of this aspect, the viscosity of the drug-containing phase may be 50 mPa·s or more. Owing to this characteristic, the formulation of the present invention can be made excellent in the storage stability in terms of difficulty in causing the change in shape. Although the reason is not clear, it is presumed because, for example, the release of the drug of the first fraction in the formulation is inhibited due to fixation of the second fraction.

The viscosity of the drug-containing phase of this aspect of the present invention is not especially limited within the above-described range, and the lower limit is preferably 50 mPa·s, more preferably 150 mPa·s, and particularly preferably 1,500 mPa·s. The upper limit of the viscosity is not especially limited, and is preferably 20,000,000 mPa·s, more preferably 15,000,000 mPa·s, and particularly preferably 10,000,000 mPa·s.

In this aspect, the viscosity means a value measured at 25° C. with a cone-plate rotational viscometer in accordance with JIS Z8803:2011 "Methods for viscosity measurement of liquid" when it is 1000 mPa·s or more, and with a rolling ball viscometer when it is lower than 1000 mPa·s.

Although this is not restrictive, the viscosity of the drug-containing phase of this aspect can be appropriately attained particularly by selecting a base.

In this aspect, the base may appropriately contain an additional component in addition to those stated above as general examples. In particular, from the viewpoint of the effect of this aspect, an additive having a gelling effect (a gelling agent) may be further contained so as to set the viscosity of the formulation to a prescribed range. Such an additive is not especially limited, and for example, hydrocarbons such as resins and silicones, amino acid, cyclic peptide, epoxy, rosin, melamine, pectins such as polysaccharides and surfactants, alginic acid, carrageenan, locust bean gum, guar gum, xanthan gum, dextrin fatty acid ester, inulin fatty acid ester, glycerin fatty acid ester and the like can be used. The resins are not especially limited, and examples include polyethylene, polypropylene, polyester, polystyrene and polyurethane. A base containing such a resin is not especially limited, and for example, a base containing such an additive in a ratio of 0.1 to 50%, preferably 1 to 30% can be used. Such a base is not especially limited, and for example, hydrocarbon-based bases such as liquid paraffin, cyclohexane, n-octane, toluene and xylene, and ester-based bases such as isopropyl myristate, isononyl isononanoate, isotridecyl isononanoate and triethylhexanoin are suitably used. A specific example of such a base is not especially limited, but includes a hydrocarbon gel ointment base such as Plastibase® (Bristol Myers Squibb) containing 95% of liquid paraffin and 5% polyethylene resin as a gelling agent.

Although this is not restrictive, a number average particle size of the particle contained in the formulation of this aspect can generally be 1 nm to 50,000 nm. From the viewpoint of persistence, transdermal absorption and the storage stability, the number average particle size of the particle contained in the formulation of the present invention is preferably 2 nm to 10,000 nm, and more preferably 3 nm to 5,000 nm.

It is noted that the number average particle size is one calculated by a dynamic light scattering method when the particle is dispersed in a solvent.

Although this is not restrictive, in the particle contained in the formulation of this aspect, a ratio between the first fraction and the second fraction (first fraction:second fraction) is preferably 1:3 to 1:100, more preferably 1:5 to 1:70, and further preferably 1:10 to 1:50 in a weight ratio from the viewpoint of the effect of the present invention.

1.1.4 Other Additive Components

The formulation of the present invention may contain other additive components in accordance with the dosage form, intended use and the like.

The additive components are not especially limited, and examples include an excipient, a colorant, a lubricant, a binder, an emulsifier, a thickener, a humectant, a stabilizer, a preservative, a solvent, a solubilizer, a suspending agent, a buffer, a pH adjuster, a gelling agent, an adhesive, an antioxidant, an absorption promoter, a stimulation reducing agent, an antiseptic, a chelating agent and a dispersant.

2. Method for Producing Formulation

Although this is not restrictive, the formulation of the present invention can be produced, for example, as follows.

Although this is not restrictive, the particle of the present invention can be first produced, for example, as follows. An active ingredient and additive components such as a stabilizer, an absorption promoter and a stimulation reducing agent, if necessary, are dissolved in pure water or a solvent such as a phosphate buffer. To the resultant, a solution obtained by dissolving, in a solvent such as cyclohexane, hexane or toluene, a surfactant and additive components such as a stimulation reducing agent, an analgesic, an absorption promoter and a stabilizer, if necessary, is added, followed by stirring with a homogenizer or the like. Thereafter, the resultant is freeze-dried or the like, and as necessary, dispersed in a solvent such as isopropyl myristate or the like, and subjected to filtration with a filter or the like, chromatography, centrifugation or the like, and thus, the particle of the present invention can be prepared. The production of the particle can be confirmed through particle size measurement or with an optical microscope.

The particle can be used for producing, for example, the following external formulation. The particle is mixed with the ester compound of the present invention and, if necessary, a base such as a liquid base or an ointment described above, and additive components such as an absorption promoter, a thickener and a gelling agent, in a prescribed ratio, and thus, a composition containing the particle is obtained. The thus obtained composition may be directly used, or in accordance with the use, may be used in a state where it is applied on or impregnated into a natural fabric member such as gauze or absorbent cotton, a synthetic fiber fabric member such as polyester or polyethylene, a woven fabric or non-woven fabric obtained by appropriately combining these members, or a transparent film, so as to be held thereon, with the resultant covered with an adhesive covering member or the like. Alternatively, the composition containing the particle may be dispersed or suspended in a component other than the base, such as water, to be used.

Another example of the method for producing the external formulation includes a solution coating method. For example, first, the particle of the present invention, the ester compound of the present invention, and if necessary, a second base, and additive components such as an absorption promoter, a thickener and a gelling agent described above are added to a solvent such as hexane, toluene or ethyl acetate in a prescribed ratio, and the resultant is stirred to prepare a homogeneous solution. A solid component concentration in the solution is preferably 10 to 80% by weight, and more preferably 20 to 60% by weight. Next, the solution containing the above-described components is uniformly applied on a release liner (such as a silicone-treated polyester film) using a coater such as a knife coater, a comma coater or a reverse coater, the resultant is dried to complete an active ingredient-containing layer, and a support is laminated on the layer to obtain the external formulation. Depending on the type of support, a release liner may be laminated on the surface of the layer after forming the layer on the support.

The external formulation thus obtained is appropriately cut, in accordance with the intended use, into an elliptical, circular, square or rectangular shape. Besides, an adhesive layer or the like may be provided in a surrounding portion if necessary.

3. Use of Formulation

The formulation of the present invention can be used in a wide range of use including external drugs and cosmetics in accordance with the type of active ingredient. Although this is not restrictive, the formulation of the present invention can be used as, for example, an external preparation such as a transdermal absorption formulation, a nasal drop, an eye drop, a suppository or an oral cavity agent. In this case, the formulation is generally persistent for several hours to 1 week, and in a preferred aspect, it is used to be applied once in a period of half a day to a week.

When the formulation of the present invention is an external drug, a target disease depends on the type of active ingredient.

Although this is not restrictive, the external formulation of the present invention is used as a tape (of reservoir type, matrix type or the like), an ointment, a lotion, an aerosol, a plaster, an aqueous poultice, a cream, a gel, an aerosol, a patch, a nasal drop, an eye drop, a suppository, an oral agent or a microneedle.

Now, the present invention will be described in detail with reference to examples and test examples, and it is noted that the present invention is not limited to these examples.

EXAMPLES

Example 1

First, 0.6 g of donepezil hydrochloride (manufactured by Tokyo Chemical Industry Co., Ltd., molecular weight: 416, water-octanol partition coefficient: 4.3) was dissolved in 40 g of pure water, and a solution obtained by dissolving 3.0 g of sucrose erucic acid ester (ER-290, manufactured by Mitsubishi-Kagaku Foods Corporation, melting point: 4.0° C., HLB: 2, containing principal components of diester and triester) in 80 g of cyclohexane was added to the resultant, followed by stirring with a homogenizer (25,000 rpm). The resultant was freeze-dried for 2 days to obtain a particle. To 0.4 g of the thus obtained particle, 9.6 g of isodecyl neopentanoate (Neolight 100P, manufactured by Kokyu Alcohol Kogyo Co., Ltd., water-octanol partition coefficient: 5.9, SP value: 7.4) was added to be mixed and dispersed to prepare an external preparation.

Example 2

An external preparation was prepared in the same manner as in Example 1 except that isodecyl neopentanoate used in Example 1 was replaced with squalane (NIKKOL Olive Squalane, manufactured by Nikko Chemicals Co., Ltd., water-octanol partition coefficient: 14.7, SP value: 7.7).

Example 3

An external preparation was prepared in the same manner as in Example 1 except that isodecyl neopentanoate used in Example 1 was replaced with octyldodecyl myristate (Exepal OD-M, manufactured by Kao Corporation, water-octanol partition coefficient: 16.0, SP value: 8.1).

Example 4

An external preparation was prepared in the same manner as in Example 1 except that the amount of donepezil hydrochloride of Example 1 was changed to 0.1 g.

Example 5

An external preparation was prepared in the same manner as in Example 2 except that the amount of donepezil hydrochloride of Example 2 was changed to 0.1 g.

Example 6

An external preparation was prepared in the same manner as in Example 3 except that the amount of donepezil hydrochloride of Example 3 was changed to 0.1 g.

Example 7

An external preparation was prepared in the same manner as in Example 2 except that the amount of donepezil hydrochloride of Example 2 was changed to 0.03 g.

Example 8

An external preparation was prepared in the same manner as in Example 3 except that the amount of donepezil hydrochloride of Example 3 was changed to 0.03 g.

Example 9

An external preparation was prepared in the same manner as in Example 1 except that donepezil hydrochloride used in Example 1 was replaced with risedronate monosodium hemipentahydrate (manufactured by Tokyo Chemical Industry Co., Ltd., molecular weight: 306, water-octanol partition coefficient: −5.0).

Example 10

An external preparation was prepared in the same manner as in Example 2 except that donepezil hydrochloride used in Example 2 was replaced with risedronate monosodium hemipentahydrate.

Example 11

An external preparation was prepared in the same manner as in Example 3 except that donepezil hydrochloride used in Example 3 was replaced with risedronate monosodium hemipentahydrate.

Example 12

An external preparation was prepared in the same manner as in Example 4 except that donepezil hydrochloride used in Example 4 was replaced with risedronate monosodium hemipentahydrate.

Example 13

An external preparation was prepared in the same manner as in Example 5 except that donepezil hydrochloride used in Example 5 was replaced with risedronate monosodium hemipentahydrate.

Example 14

An external preparation was prepared in the same manner as in Example 6 except that donepezil hydrochloride used in Example 6 was replaced with risedronate monosodium hemipentahydrate.

Example 15

An external preparation was prepared in the same manner as in Example 7 except that donepezil hydrochloride used in Example 7 was replaced with risedronate monosodium hemipentahydrate.

Example 16

An external preparation was prepared in the same manner as in Example 8 except that donepezil hydrochloride used in Example 8 was replaced with risedronate monosodium hemipentahydrate.

Comparative Example 1

An external preparation was prepared in the same manner as in Example 1 except that the amount of donepezil hydrochloride of Example 1 was changed to 0.02 g.

Comparative Example 2

An external preparation was prepared in the same manner as in Comparative Example 1 except that donepezil hydrochloride used in Comparative Example 1 was replaced with risedronate monosodium hemipentahydrate.

Comparative Example 3

An external preparation was prepared in the same manner as in Example 1 except that the amount of donepezil hydrochloride of Example 1 was changed to 1.0 g.

Comparative Example 4

An external preparation was prepared in the same manner as in Example 3 except that the amount of donepezil hydrochloride of Example 3 was changed to 1.0 g.

Comparative Example 5

An external preparation was prepared in the same manner as in Example 1 except that the amount of donepezil hydrochloride of Example 1 was changed to 0.006 g.

Comparative Example 6

An external preparation was prepared in the same manner as in Example 3 except that the amount of donepezil hydrochloride of Example 3 was changed to 0.006 g.

Test Example 1 Shape Stability Test

In each of the external preparations prepared in Examples 1 to 16 and Comparative Examples 1 to 6, the number average particle size was calculated by the dynamic light scattering method (Zetasizer Nano S, manufactured by Spectris Co., Ltd.).

Examination results of the number average particle sizes of the various external preparations are shown in Table 1.

All the preparations of Examples had a number average particle size of 1 to 500 nm, and the particles were found to be formed therein. On the other hand, in all Comparative Examples, the number average particle size was smaller than 1 nm probably because the particles had been dissolved, or could not be measured because crystal of the drug was precipitated ("Good" means a number average particle size of 1 nm to 500 nm, and "Poor" means unmeasurable).

TABLE 1

| Example 1 | Example 2 | Example 3 | Example 4 | Example 5 | Example 6 | Example 7 | Example 8 |
|---|---|---|---|---|---|---|---|
| Good | Good | Good | Good | Good | Good | Good | Good |
| Example 9 | Example 10 | Example 11 | Example 12 | Example 13 | Example 14 | Example 15 | Example 16 |
| Good | Good | Good | Good | Good | Good | Good | Good |
| Comparative Example 1 | Comparative Example 2 | Comparative Example 3 | Comparative Example 4 | Comparative Example 5 | Comparative Example 6 | | |
| Poor | Poor | Poor | Poor | Poor | Poor | | |

Example 17

First, 0.1 g of memantine hydrochloride (manufactured by Tokyo Chemical Industry Co., Ltd., molecular weight: 216, water-octanol partition coefficient: 0.3) was dissolved in 40 g of pure water, and a solution obtained by dissolving 0.5 g of sucrose erucic acid ester in 80 g of cyclohexane was added to the resultant, followed by stirring with a homogenizer (25,000 rpm). The resultant was freeze-dried for 2 days to obtain a particle. To 25 mg of the thus obtained particle, 75 mg of isopropyl myristate (IPM, manufactured by Kokyu Alcohol Kogyo Co., Ltd., water-octanol partition coefficient: 7.2, SP value: 8.3) was added to be mixed and dispersed to prepare an external preparation.

Example 18

A particle was prepared in the same manner as in Example 17 except that the amount of sucrose erucic acid ester was changed to 1.5 g, so as to obtain an external preparation in the same manner as in Example 17.

Example 19

A particle was prepared in the same manner as in Example 17 except that the amount of sucrose erucic acid ester was changed to 3.0 g, so as to obtain an external preparation in the same manner as in Example 17.

Example 20

A particle was prepared in the same manner as in Example 17 except that the amount of sucrose erucic acid ester was changed to 5.0 g, so as to obtain an external preparation in the same manner as in Example 17.

Example 21

A particle was prepared in the same manner as in Example 17 except that the amount of sucrose erucic acid ester was changed to 10.0 g, so as to obtain an external preparation in the same manner as in Example 17.

Example 22

A particle was prepared in the same manner as in Example 17 except that sucrose erucic acid ester was replaced with 5.0 g of sucrose lauric acid ester (L-195, manufactured by Mitsubishi-Kagaku Foods Corporation, melting point: 23.9° C., HLB: 2, containing principal components of diester and triester), so as to obtain an external preparation in the same manner as in Example 17.

Example 23

To 15 mg of the particle obtained in Example 19, 85 mg of isononyl isononanoate (KAK99, manufactured by Kokyu Alcohol Kogyo Co., Ltd., water-octanol partition coefficient: 6.5, SP value: 8.2, difference in the number of carbon atoms between the longest and shortest portions in the longest straight-chain alkyl group portion: 0) was added to be mixed and dispersed to prepare an external preparation.

Example 24

To 15 mg of the particle obtained in Example 19, 85 mg of isotridecyl isononanoate (KAK139, manufactured by Kokyu Alcohol Kogyo Co., Ltd., water-octanol partition coefficient: 9.2, SP value: 8.2, difference in the number of carbon atoms between the longest and shortest portions in the longest straight-chain alkyl group portion: 4) was added to be mixed and dispersed to prepare an external preparation.

Example 25

To 15 mg of the particle obtained in Example 19, 85 mg of neopentyl glycol diisononanoate (NPDIN, manufactured by Kokyu Alcohol Kogyo Co., Ltd., water-octanol partition coefficient: 7.2, SP value: 6.7, difference in the number of carbon atoms between the longest and shortest portions in the longest straight-chain alkyl group portion: 0) was added to be mixed and dispersed to prepare an external preparation.

Example 26

To 15 mg of the particle obtained in Example 19, 85 mg of triethylhexanoin (TOG, manufactured by Kokyu Alcohol Kogyo Co., Ltd., water-octanol partition coefficient: 8.9, SP value: 8.9, difference in the number of carbon atoms between the longest and shortest portions in the longest straight-chain alkyl group portion: 0) was added to be mixed and dispersed to prepare an external preparation.

Example 27

To 15 mg of the particle obtained in Example 19, 85 mg of isodecyl neopentanoate was added to be mixed and dispersed to prepare an external preparation.

Example 28

To 15 mg of the particle obtained in Example 19, 85 mg of soy oil (Wako Pure Chemical Industries, Ltd., water-octanol partition coefficient: 6.3, SP value: 8.2) was added to be mixed and dispersed to prepare an external preparation.

Example 29

First, 0.1 g of verdenafil hydrochloride hydrate (manufactured by Atomax, molecular weight: 579, water-octanol partition coefficient: 0.0) was dissolved in 40 g of pure water, and a solution obtained by dissolving 1.0 g of sucrose erucic acid ester in 80 g of cyclohexane was added to the resultant, followed by stirring with a homogenizer (25,000 rpm). The resultant was freeze-dried for 2 days to obtain a particle. To 15 mg of the thus obtained particle, 85 mg of isononyl isononanoate (KAK99, manufactured by Kokyu Alcohol Kogyo Co., Ltd., SP value: 8.2, difference in the number of carbon atoms between longest and shortest portion in the longest straight-chain alkyl group portion: 0) was added to be mixed and dispersed to prepare an external preparation.

Example 30

To 15 mg of the particle obtained in Example 29, 85 mg of isotridecyl isononanoate (KAK139, manufactured by Kokyu Alcohol Kogyo Co., Ltd., SP value: 8.2, difference in the number of carbon atoms between the longest and shortest portions in the longest straight-chain alkyl group portion: 4) was added to be mixed and dispersed to prepare an external preparation.

Example 31

To 15 mg of the particle obtained in Example 29, 85 mg of neopentyl glycol diisononanoate (NPDIN, manufactured by Kokyu Alcohol Kogyo Co., Ltd., SP value: 6.7, difference in the number of carbon atoms between the longest and shortest portions in the longest straight-chain alkyl group portion: 0) was added to be mixed and dispersed to prepare an external preparation.

Example 32

To 15 mg of the particle obtained in Example 29, 85 mg of triethylhexanoin (TOG, manufactured by Kokyu Alcohol Kogyo Co., Ltd., SP value: 8.9, difference in the number of carbon atoms between the longest and shortest portions in the longest straight-chain alkyl group portion: 0) was added to be mixed and dispersed to prepare an external preparation.

Example 33

First, 0.1 g of donepezil hydrochloride was dissolved in 40 g of pure water, and a solution obtained by dissolving 1.0 g of sucrose erucic acid ester in 80 g of cyclohexane was added thereto, followed by stirring with a homogenizer (25,000 rpm). The resultant was freeze-dried for 2 days to obtain a particle. To 15 mg of the thus obtained particle, 85 mg of isononyl isononanoate was added to be mixed and dispersed to prepare an external preparation.

Example 34

To 15 mg of the particle obtained in Example 33, 85 mg of isotridecyl isononanoate (KAK139, manufactured by Kokyu Alcohol Kogyo Co., Ltd., SP value: 8.2, difference in the number of carbon atoms between the longest and shortest portions in the longest straight-chain alkyl group portion: 4) was added to be mixed and dispersed to prepare an external preparation.

Example 35

To 15 mg of the particle obtained in Example 33, 85 mg of neopenyl glycol diisononanoate (NPDIN, manufactured by Kokyu Alcohol Kogyo Co., Ltd., SP value: 6.7, difference in the number of carbon atoms between the longest and shortest portions in the longest straight-chain alkyl group portion: 0) was added to be mixed and dispersed to prepare an external preparation.

Example 36

To 15 mg of the particle obtained in Example 33, 85 mg of triethylhexanoin (TOG, manufactured by Kokyu Alcohol Kogyo Co., Ltd., SP value: 8.9, difference in the number of carbon atoms between the longest and shortest portions in the longest straight-chain alkyl group portion: 0) was added to be mixed and dispersed to prepare an external preparation.

Comparative Example 7

A particle was prepared in the same manner as in Example 17 except that the amount of sucrose erucic acid ester was changed to 0.3 g, so as to obtain an external preparation in the same manner as in Example 17.

Comparative Example 8

An external preparation was obtained in the same manner as in Comparative Example 7 except that sucrose erucic acid ester was replaced with polyglycerin oleic acid ester (O-50D, manufactured by Mitsubishi-Kagaku Foods Corporation, HLB: 7).

Example 37

An external preparation was prepared by adding 50 mg of Plastibase® (manufactured by Taisho Pharmaceutical Co., Ltd.) to 50 mg of the particle obtained in Example 19 to be mixed and dispersed therein.

Example 38

An external preparation was prepared by adding 60 mg of Plastibase® (manufactured by Taisho Pharmaceutical Co., Ltd.) to 40 mg of the particle obtained in Example 19 to be mixed and dispersed therein.

Example 39

An external preparation was prepared by adding 70 mg of Plastibase® (manufactured by Taisho Pharmaceutical Co., Ltd.) to 30 mg of the particle obtained in Example 19 to be mixed and dispersed therein.

Example 40

An external preparation was prepared by adding 90 mg of Plastibase® (manufactured by Taisho Pharmaceutical Co., Ltd.) to 10 mg of the particle obtained in Example 19 to be mixed and dispersed therein.

Example 41

To 60 mg of the particle obtained in Example 19, 40 mg of a gel, which was obtained by adding 15% by weight of dextrin palmitate (Rheopearl® KL2, manufactured by Chiba Flour Milling Co., Ltd.) to isopropyl myristate to be dissolved at 120° C., and allowing the resultant to stand still at room temperature overnight, was added to be mixed and dispersed therein to prepare an external preparation.

Example 42

An external preparation was prepared by adding 25 mg of olive oil (manufactured by Wako Pure Chemical Industries, Ltd., water-octanol partition coefficient: 7.6, SP value: 8.4) to 75 mg of the particle obtained in Example 19 to be mixed and dispersed therein.

Example 43

An external preparation was prepared by adding 25 mg of liquid paraffin (manufactured by Wako Pure Chemical Industries, Ltd., density: 0.800 to 0.835 mg/ml, water-octanol partition coefficient: 7.2, SP value: 8.2) to 75 mg of the particle obtained in Example 19 to be mixed and dispersed therein.

Example 44

An external preparation was prepared by adding 25 mg of Japanese pharmacopoeial light liquid paraffin (manufactured by Kaneda Co. Ltd., density: 0.830 to 0.843 mg/ml, water-octanol partition coefficient: 8.3, SP value: 8.1) to 75 mg of the particle obtained in Example 19 to be mixed and dispersed therein.

The stability of the respective external preparations produced in Examples 17 to 36 and Comparative Examples 7 and 8 was checked using an optical microscope (Eclipse® ME600, manufactured by Nikon Corporation) (200× magnification) with the shape of each preparation used as a parameter.

The shape of each preparation having been allowed to stand at 25° C. or 40° C. for 3 days to 1 month was compared with the initial shape to be evaluated based on indices of the following criteria, and the results are shown in Table 2.
(Shape Evaluation Criteria)
Good: not changed
Fair: partially changed
Poor: changed Table 3 shows results of measured viscosities and stabilities of the external preparations produced in Examples 37 to 45. Incidentally, the viscosity was measured with respect to 1 g of each external preparation in accordance with JIS Z8803 (2011) by a zero method at 25° C. Besides, the stability was checked using an optical microscope with the shape of the formulation used as a parameter.

The shape of the preparation having been allowed to stand at 40° C. for 1 week was compared with the initial shape, and the following evaluation criteria were used as indices.

(Shape Evaluation Criteria)
Good: not changed
Fair: rather changed
Poor: changed

TABLE 2

|  | 25° C./ 3 days | 25° C./ 7 days | 40° C./ 7 days | 40° C./ 30 days |
|---|---|---|---|---|
| Example 17 | Fair | | | |
| Example 18 | Good | | | |
| Example 19 | Good | Poor | Poor | |
| Example 20 | Good | | | |
| Example 21 | Fair | | | |
| Example 22 | Fair | | | |
| Example 23 | | Good | | |
| Example 24 | | Good | | |
| Example 25 | | Good | | |
| Example 26 | | Good | | |
| Example 27 | Fair | Poor | | |
| Example 28 | Fair | Poor | | |
| Example 29 | | | Good | Good |
| Example 30 | | | Good | Good |
| Example 31 | | | Good | Good |
| Example 32 | | | Good | Good |
| Example 33 | | | Good | Fair |
| Example 34 | | | Good | Good |
| Example 35 | | | Good | Fair |
| Example 36 | | | Good | Good |
| Comparative Example 7 | Poor | | | |
| Comparative Example 8 | Poor | | | |

TABLE 3

|  | Viscosity (mPa·s) | 40° C./ 7 days | 40° C./ 30 days |
|---|---|---|---|
| Example 37 | 3207 | Good | Good |
| Example 38 | 3515 | Good | Good |
| Example 39 | 5314 | Good | Good |
| Example 40 | 6800 | Good | Good |
| Example 41 | 1800 | Good | Good |
| Example 42 | 99 | Fair | Poor |
| Example 43 | <20 | Good | Fair |
| Example 44 | 56 | Good | Good |

Example 45

First, 0.1 g of montelukast sodium was dissolved in 40 g of pure water, and a solution obtained by dissolving 1.0 g of sucrose erucic acid ester and 1.0 g of sucrose stearic acid ester (S-070, manufactured by Mitsubishi-Kagaku Foods Corporation, melting point: 61.5° C., HLB: 1 or less, containing principal components of diester and triester) in 80 g of cyclohexane was added thereto, followed by stirring (10,000 rpm, 2 minutes) with a homogenizer (PT3100, manufactured by Polytron) at 25° C. The resultant was freeze-dried by a freeze-drier (FDU2110, manufactured by Tokyo Rikakikai Co., Ltd.) for 2 days to obtain a particle. Three g of the thus obtained particle was added to 17.0 g of isopropyl myristate to obtain a suspension.

Example 46

A suspension was obtained in the same manner as in Example 45 except that the amount of sucrose erucic acid ester was changed to 2.0 g.

Example 47

A suspension was obtained in the same manner as in Example 45 except that the amount of sucrose erucic acid ester was changed to 2.5 g and that the amount of sucrose stearic acid ester was changed to 0.5 g.

Example 48

A suspension was obtained in the same manner as in Example 45 except that the amount of sucrose erucic acid ester was changed to 2.75 g and that the amount of sucrose stearic acid ester was changed to 0.25 g.

Example 49

A suspension was obtained in the same manner as in Example 45 except that the amount of sucrose erucic acid ester was changed to 2.9 g and that the amount of sucrose stearic acid ester was changed to 0.1 g.

Example 50

A suspension was obtained in the same manner as in Example 49 except that sucrose stearic acid ester was replaced with S-170 (manufactured by Mitsubishi-Kagaku Foods Corporation, melting point: 65.2° C., HIB: 1, containing principal components of diester and triester).

Comparative Example 9

Although it was tried to obtain a suspension in the same manner as in Example 45 except that the amount of sucrose erucic acid ester was changed to 0.2 g and that the amount of sucrose stearic acid ester was changed to 0.1 g, a suspension in which a particle was finely dispersed could not be obtained.

Samples obtained in Examples 45 to 50 and Comparative Example 9 were visually observed, resulting in finding that a suspension in which a particle was finely dispersed could be obtained in each of Examples 45 to 50. In Comparative Example 9, however, a particle in which a particle was finely dispersed could not be obtained.

The invention claimed is:
1. A formulation comprising:
   a particle comprising a core portion containing at least one active ingredient and a shell portion containing at least one surfactant; and
   a base,
   wherein the active ingredient contains a compound having a hydrophilic group and a hydrophobic group, and
   the surfactant contains a surfactant having a melting point of 30° C. or more and a surfactant having a melting point of lower than 30° C.
2. The formulation according to claim 1, wherein the base has a water-octanol partition coefficient of 6.5 to 17.0.
3. The formulation according to claim 1,
   wherein the base contains:
   (a) an ester compound containing at least two, in total, hydrocarbon groups, each having 5 or more carbon atoms in a longest straight-chain portion thereof, of at least one selected from the group consisting of an alkyl group, an alkenyl group and an alkynyl group, a difference in the number of carbon atoms, in the longest straight-chain portion thereof among the hydrocarbon groups, respectively having longest and shortest longest straight-chain portions being smaller than 5; and/or (b) a hydrocarbon having 12 or more carbon atoms.

4. The formulation according to claim 3, wherein the ester compound and the hydrocarbon have a solubility parameter (SP value) of 6.5 to 10 $(cal/cm^3)^{1/2}$.

5. The formulation according to claim 3, wherein the ester compound is at least one ester compound selected from the group consisting of isononanoic acid esters, triglycerides and glycol fatty acid esters.

6. The formulation according to claim 3, wherein the ester compound is at least one ester compound selected from the group consisting of isononyl isononanoate, isotridecyl isononanoate, neopentyl glycol diisononanoate, triethylhexanoin and triheptanoin.

7. The formulation according to claim 1, wherein the surfactant has a weighted average value of an HLB value of 10 or less.

8. The formulation according to claim 1, wherein the surfactant has an alkyl chain.

9. The formulation according to claim 1, wherein the surfactant is at least one surfactant selected from the group consisting of sucrose fatty acid esters, glycerin fatty acid esters, polyoxyethylene glycerin fatty acid esters, sorbitan fatty acid esters, polyoxyethylene sorbitol fatty acid esters, polyoxyethylene castor oil and hydrogenated castor oil.

10. The formulation according to claim 1, wherein the surfactant having a melting point of 30° C. or more is a sucrose fatty acid ester.

11. The formulation according to claim 10, wherein the sucrose fatty acid ester is an ester of a sucrose and a saturated or unsaturated monovalent fatty acid having 8 to 30 carbon atoms.

12. The formulation according to claim 10, wherein the sucrose fatty acid ester is at least one sucrose fatty acid ester selected from the group consisting of sucrose palmitic acid esters, sucrose oleic acid esters and sucrose behenic acid esters.

13. The formulation according to claim 1,
wherein the active ingredient contains a readily crystallizable compound, and
the surfactant contains a surfactant having a melting point of −40° C. or more in a ratio of 5 to 100 parts by weight based on 1 part by weight of the readily crystallizable compound.

14. The formulation according to claim 13, wherein the surfactant is a sucrose fatty acid ester.

15. The formulation according to claim 14, wherein the sucrose fatty acid ester is an ester of a sucrose and a saturated and/or unsaturated monovalent fatty acid having 8 to 30 carbon atoms.

16. The formulation according to claim 14, wherein the sucrose fatty acid ester is at least one sucrose fatty acid ester selected from sucrose lauric acid esters, sucrose oleic acid esters and sucrose erucic acid esters.

17. The formulation according to claim 1,
wherein the base contains:
an ester compound containing at least two, in total, hydrocarbon groups, each having 5 or more carbon atoms in a longest straight-chain portion thereof, of at least one selected from the group consisting of an alkyl group, an alkenyl group and an alkynyl group, a difference in the number of carbon atoms, in the longest straight-chain portion thereof among the hydrocarbon groups, respectively having longest and shortest longest straight-chain portions being smaller than 5, and
the ester compound is at least one ester compound selected from the group consisting of isononyl isononanoate, isotridecyl isononanoate, neopentyl glycol diisononanoate and triethylhexanoin.

* * * * *